(12) United States Patent
Gilbertson et al.

(10) Patent No.: US 9,856,485 B2
(45) Date of Patent: *Jan. 2, 2018

(54) RECOMBINANT DNA CONSTRUCTS EMPLOYING SITE-SPECIFIC RECOMBINATION

(71) Applicant: Monsanto Technology LLC, St. Louis, MO (US)

(72) Inventors: Larry A. Gilbertson, Chesterfield, MO (US); Shihshieh Huang, Woodland, CA (US); Thomas Malvar, North Stonington, CT (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 606 days.

This patent is subject to a terminal disclaimer.

(21) Appl. No.: 14/337,932

(22) Filed: Jul. 22, 2014

(65) Prior Publication Data

US 2014/0338010 A1 Nov. 13, 2014

Related U.S. Application Data

(63) Continuation of application No. 12/869,806, filed on Aug. 27, 2010, now Pat. No. 8,816,153.

(51) Int. Cl.
*C12N 15/82* (2006.01)
*C12N 15/63* (2006.01)

(52) U.S. Cl.
CPC ......... *C12N 15/8213* (2013.01); *C12N 15/63* (2013.01); *C12N 15/8217* (2013.01); *C12N 15/8218* (2013.01); *C12N 15/8243* (2013.01)

(58) Field of Classification Search
None
See application file for complete search history.

(56) References Cited

U.S. PATENT DOCUMENTS

| 6,723,896 | B1 | 4/2004 | Moller et al. | |
|---|---|---|---|---|
| 6,933,146 | B2* | 8/2005 | Helliwell | C12N 15/10 435/320.1 |
| 8,816,153 | B2* | 8/2014 | Gilbertson | C12N 15/63 435/320.1 |
| 2005/0130919 | A1* | 6/2005 | Xu | C12N 15/111 514/44 A |

OTHER PUBLICATIONS

Borne et al 1994 (Molecular and General Genetics 243:6 p. 613-621).*
Mylnarova et al. (Transgen. Res. (2003) 12: 45-57).*
Hunter et al., "Maize Opaque Endosperm Mutation Create Extensive Changes in Patterns of Gene Expression," *The Plant Cell*, 14:2591-2612 (2002).
Mlynárová et al., "A self-excising Cre recombinase allows efficient recombination of multiple ectopic heterospecific lox sites in transgenic tobacco," *Transgenic Research*, 12:45-57 (2003).

* cited by examiner

*Primary Examiner* — Matthew Keogh
(74) *Attorney, Agent, or Firm* — Amanda Carmany-Rampey; David R. Marsh; Arnold & Porter Kaye Scholer LLP

(57) ABSTRACT

Recombinant DNA constructs, for use in plants and plant cells, have site-specific recombination sites that allow assessing phenotypes and modes of action by over expression or suppression of endogenous genes. In an aspect, a single DNA construct can be switched between over expression and suppression by the action of a recombinase such as the Cre recombinase on constructs having lox recombination sites. Other useful recombination systems include the Flp/frt system, the R/Rs system, the Dre/rox system, and the GIN/gix system.

21 Claims, 9 Drawing Sheets

RECOMBINANT DNA CONSTRUCTS EMPLOYING SITE-SPECIFIC RECOMBINATION

CROSS REFERENCE TO RELATED APPLICATIONS

This application claims the benefit of U.S. Non-Provisional patent application Ser. No. 12/869,806, filed on Aug. 27, 2010, which is incorporated herein by reference in its entirety.

FIELD OF THE INVENTION

Disclosed herein are recombinant DNA constructs utilizing site-specific recombination technology and methods of making and using such constructs.

BACKGROUND OF THE INVENTION

The study of gene mode of action and effect of phenotype in plants often employs transgenic plants that over express an transgenic gene and transgenic plants that suppress a endogenous gene where the plants are transformed using vectors to insert recombinant DNA constructs for regulating endogenous plant genes are designed to either over express the gene or to suppress the gene. Likewise, transgenic plants with the recombinant DNA construct to either over express or suppress the gene in plants are made with separate constructs that may not provide comparative traits due to interactions from transgene insertions at different chromosomal loci.

SUMMARY OF THE INVENTION

Mode of action studies are better made using a single construct inserted in one chromosomal locus that can be switched between expression and suppression of an endogenous gene. The invention provides recombinant DNA constructs for assessing both suppression and expression of an endogenous gene. More specifically, the recombinant DNA constructs comprise a promoter operably linked to sense-oriented DNA encoding an endogenous protein. The dual function of the recombinant DNA constructs is made possible by the presence of at least one fragment of the DNA encoding the endogenous protein in the anti-sense orientation and a pair of recombination sites which are recognized by a site-specific recombinase. At least one of the recombination sites is located between the DNA encoding an endogenous protein and the antisense fragment. The location of the other recombination site of the pair can vary depending of the design as illustrated below. The recombinant DNA constructs also comprises DNA providing a polyadenylation sequence.

As illustrated herein depending of the design, stable integration of a recombinant DNA construct into plant cells results in either expression or suppression of the DNA encoding an endogenous protein. Introduction of a recombinase that recognizes the recombination sites switches to the alternative function of the construct. A plant comprising a recombinant DNA construct of this invention will, depending on design, have an original function that either expresses an endogenous gene or suppresses the endogenous gene. When a plant is transformed with a vector containing this construct and then crossed with a plant containing a recombinase that recognizes the recombination sites, recombinase-mediated excision will remove the DNA between the recombination sites allowing for a change in original function. For instance, when the original function is suppression of the endogenous gene the presence of recombinase will switch the function to allow expression of DNA encoding the endogenous protein.

In one aspect the recombinant DNA construct comprises a spacer that is located between the pair of recombination sites. The spacer has a length sufficient to prevent fold back and self-hybridization in RNA transcribed from the recombinant DNA construct to maintain expression of the DNA encoding the endogenous protein. Any of a number of site recognizing recombinases can be used in the practice of this invention including Cre recombinase with lox sites, Flp recombinase with frt sites, R recombinase with R sites, Dre recombinase with rox sites and Gin recombinase with gix sites. When a transformed plant containing this construct is crossed to a plant expressing Cre recombinase, Cre-mediated recombination at the first pair recombination sites will remove the spacer and will switch the function to allow suppression of DNA encoding the endogenous protein.

In aspects of the invention the recombinant DNA constructs further comprise DNA for one or more other elements, such as DNA encoding a selectable marker, DNA encoding a recombinase and/or DNA for a second pair of site-specific recombination sites. The DNA for encoding selectable marker, DNA encoding the recombinase or both can be located either between the first pair of site-specific recombination sites or second pair of site-specific recombination sites or both. One important aspect of the invention that a promoter operably linked to DNA encoding the recombinase is not constitutive. Useful promoters are chemically inducible promoters that are regulated by external agent. Stable integration of a recombinant DNA construct into plant cells results in suppression the DNA encoding protein and allow evaluation of suppression. When a transformed plant contains DNA for a selectable marker between recognition sites, e.g. between a second pair of recognition sites, is crossed to a plant expressing a recombinase either of the pairs of the recombination sites can be involved in recombination, recombination at the second pair of recombination sites will remove the DNA for the selectable marker allowing marker free suppression of the protein When a transformed plant contains antisense DNA encoding the endogenous protein and DNA for a selectable marker between recognition sites, e.g. between a first pair of recognition sites, is crossed to a plant expressing a recombinase, recombination at the first pair of recombination sites will remove antisense DNA encoding the endogenous protein and DNA for the selectable marker allowing marker free expression.

When a transformed plant contains DNA for a selectable marker and DNA for a recombinase between recognition sites, e.g. between a second pair of recognition sites, expressing the recombinase either of the pairs of the recombination sites can be involved in recombination, recombination at the second pair of recombination sites will remove the DNA for the selectable marker and DNA for the recombinase allowing marker free suppression of the protein. When a transformed plant contains antisense DNA for a endogenous protein, DNA for the selectable marker and DNA for the recombinase between recognition sites, e.g. between a first pair of recognition sites, expressing the recombinase, recombination at the first pair of recombination sites will remove antisense DNA for endogenous protein, DNA for the selectable marker and DNA for the recombinase allowing marker free expression. In one aspect transformed plant contains DNA for a recombinase operably linked to a constitutive promoter between recognition sites, e.g. between a second pair of recognition sites, expressing the recombinase either of the pairs of the recombination sites can be involved in recombination, recombination at the second pair of recombination sites will remove the DNA for the recombinase allowing suppression of the protein with selectable marker. When transformed plant contains antisense DNA for a endogenous protein, DNA for the recombinase between recognition sites, e.g. between a first pair of recognition sites, expressing a recombinase, recombination at the first pair of recombination sites will remove antisense DNA for endogenous protein and DNA for the recombinase allowing expression of the protein with selectable marker.

In another aspect the recombinant DNA constructs further comprise an inverted repeat of a DNA that serves as a screenable marker which DNA is located adjacent to the antisense fragment. In useful aspects of the invention the inverted repeat DNA functions to suppress a gene that provides a visible phenotype, e.g. DNA for suppressing the opaque 2 gene. Stable integration of recombinant DNA into plant/cells will allow a visual phenotype indicating desired suppression of DNA encoding for a detectable marker. In some aspects of the invention the DNA for encoding selectable marker and DNA encoding site specific recombinase are located between the second pair of site-specific recombination sites and the antisense fragment, the inverted repeat of DNA encoding for a screenable marker, DNA for encoding selectable marker and DNA encoding a site specific recombinase are located between the first pair of site-specific recombination sites. In other aspects of the invention the DNA encoding site specific recombinase is located between the second pair of site-specific recombination sites and the antisense fragment, the inverted repeat of DNA encoding for a screenable marker, and DNA encoding a site specific recombinase are located between the first pair of site-specific recombination sites.

This invention provides a method for generating a transformed plant cell and plant. This invention also provides a method for generating progeny plant seed by crossing a first plant containing the recombinant DNA construct with a second plant containing DNA expressing the first site specific recombinase to produce a population of seed that will produce plants that will express DNA encoding protein and plants that will suppress the production of said protein with or without a selectable marker.

BRIEF DESCRIPTION OF THE DRAWINGS

FIGS. 1-4 illustrate the design of recombinant DNA constructs and their use as described in the Examples. FIG. 1a depicts a recombinant DNA construct containing a promoter (P) operably linked to a DNA having a nucleotide sequence of interest (SOI) encoding a protein of interest for expression or suppression, a fragment in antisense orientation of the SOI having at least 21 nt, a pair of loxP recombination sites surrounding and bracketing the antisense fragment, and a DNA element providing polyadenylation sequence (T). FIG. 1b depicts an alternative arrangement of the construct shown in FIG. 1a where the promoter (P) is followed by the antisense fragment and then the SOI, wherein a pair of recombination (loxP) sites bracket the antisense fragment. FIG. 1c depicts a recombinant DNA construct containing a promoter (P) operably linked to the SOI, a loxP recombination site, a DNA element providing a first polyadenylation sequence (T1), a spacer with a length sufficient to prevent fold back and self-hybridization in RNA transcribed from the recombinant DNA construct, a second loxP recombination site, an antisense fragment of the SOI having at least 21 nt, and a DNA element providing a second polyadenylation sequence (T2), wherein the pair of loxP recombination sites brackets the polyadenylation sequence T1 and the spacer. FIG. 2a depicts a recombinant DNA construct with two expression cassettes, wherein the construct contains a promoter (P1) operably linked to the SOI, a first loxP recombination site, an antisense fragment of the SOI, DNA providing a first polyadenylation sequence (T1), a first lox511 recombination site, a second promoter (P2) operably linked to a DNA encoding a selectable marker, a second loxP recognition site, DNA providing a second polyadenylation sequence (T2), and a second lox511 recognition site, wherein the first pair of recombination (loxP) sites brackets the antisense fragment, the first polyadenylation sequence (T1), the first lox511 site, the second promoter (P2) and the DNA encoding selectable marker, and wherein the second pair of recombination (lox511) sites brackets the selectable marker expression cassette and the second loxP site. FIG. 2b depicts a recombinant DNA construct similar to that of FIG. 2a but having an additional DNA encoding a screenable marker (e.g., an inverted repeat of DNA for suppressing a corn opaque 2 gene). FIG. 3a depicts a recombinant DNA construct containing 3 cassettes: a promoter (P1) operably linked to the SOI, a loxP recombination site, antisense fragment of the SOI, DNA providing a first polyadenylation sequence (T1), a lox511 recombination site, a second promoter (P2) operably linked to a DNA encoding a selectable marker, DNA providing a second polyadenylation sequence (T2), a third promoter (P3) that is non-constitutive and is operably linked to DNA encoding a Cre recombinase, second loxP recombination site, DNA providing a third polyadenylation sequence (T3), and a second lox511 recognition site. The first pair of recombination sites (the loxP sites) brackets the antisense fragment, the first polyadenylation sequence (T1), the first lox511 site, the selectable marker expression cassette, the third promoter (P3) and the DNA encoding for Cre recombinase. The second pair of recombination sites (the lox511 sites) brackets the selectable marker expression cassette, the Cre recombinase expression cassette, and the second loxP site. FIG. 3b depicts a recombinant DNA construct similar to that of FIG. 3a but having an additional DNA encoding a screenable marker (e.g., an inverted repeat of DNA for suppressing a corn opaque 2 gene located adjacent to the antisense fragment). FIG. 4a depicts a recombinant DNA construct containing three cassettes: a promoter (P1) operably linked to the SOI, a first loxP recombination site, an antisense fragment of the SOI, DNA providing a first polyadenylation sequence (T1), a first lox511 recombination site, a constitutive promoter (P3) operably linked to DNA encoding a Cre recombinase, a second loxP recombination site, DNA providing a third polyadenylation sequence (T3), a second lox511 recognition site, a promoter (P2) operably linked to a DNA encoding a selectable marker, and DNA providing a second polyadenylation sequence (T2). The first pair of recombination sites (the loxP sites) brackets the antisense fragment, the first polyadenylation sequence (T1), the first lox511 site, the constitutive promoter (P3), and the DNA encoding for Cre recombinase. The second pair of recombination sites (the lox511 sites) brackets the Cre recombinase expression cassette and the second loxP site. FIG. 4b depicts a recombinant DNA construct similar to that of FIG. 4a but having an additional DNA encoding a screenable marker (e. g., an inverted repeat of DNA for suppressing a corn opaque 2 gene located adjacent to the antisense fragment).

DETAILED DESCRIPTION

Figure 1A:
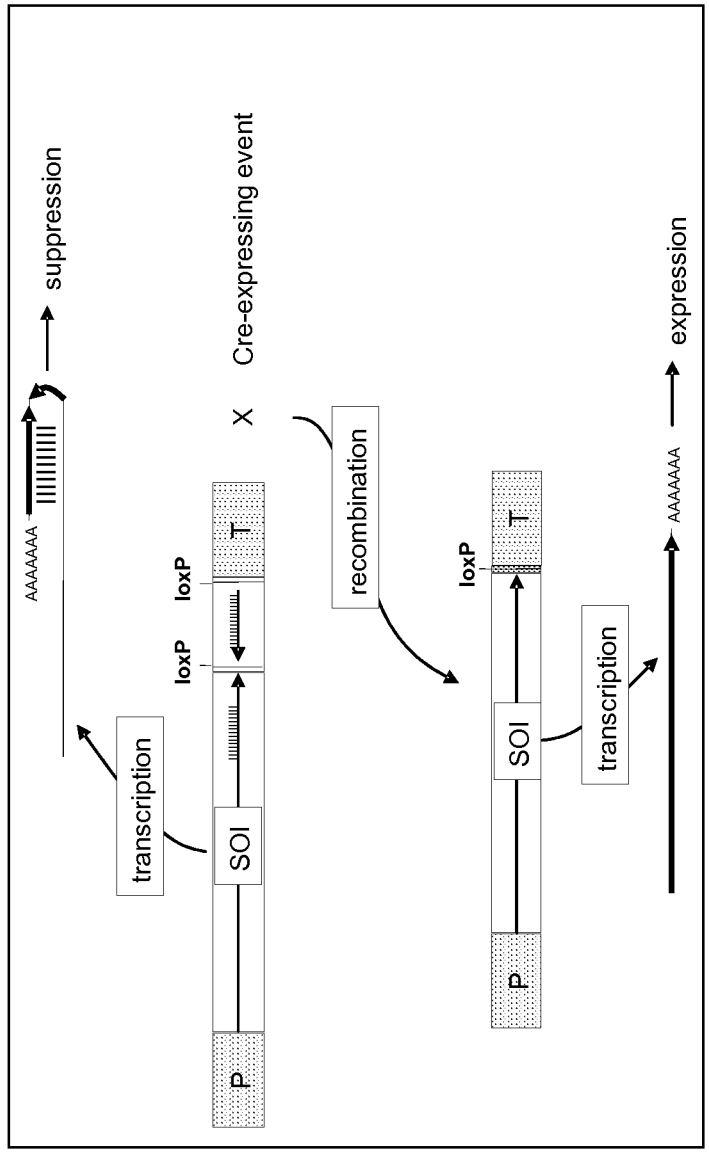
FIGS. 1a, 1b, and 1c are described in detail in Example 1.

As used herein, the term "recombinant DNA construct" means a man-made, non-natural DNA molecule.

As used herein, the term "promoter" means a DNA molecule that is involved in recognition and binding of RNA polymerase, commonly an RNA polymerase II, and other proteins (such as trans-acting transcription factors) to initiate transcription. Promoters may be defined as constitutive, i.e. generally always active, and or as inducible i.e. conditionally active i.e. active in presence of certain exogenous component A promoter may be initially isolated from the 5' untranslated region (5' UTR) of a genomic copy of a gene. Alternately, promoters may be synthetically produced or manipulated DNA molecules. Promoter fragments may exhibit promoter activity and may be useful in the recombinant DNA constructs of the invention.

As used herein, the term "3' transcription termination molecule" refers to a DNA molecule that is used during transcription to produce the 3' untranslated region (3' UTR) of an messenger RNA (mRNA) molecule. The 3' untranslated region of an mRNA molecule may be generated by specific cleavage and 3' polyadenylation producing what is known as a polyA tail. A 3' UTR may be operably linked to and located downstream of a DNA encoding protein and may include polynucleotides that provide a polyadenylation signal and other regulatory signals capable of affecting transcription, mRNA processing, or gene expression. PolyA tails are thought to function in mRNA stability and in initiation of translation.

As used herein, the term "marker" means any DNA molecule that allows the identification of the presence of recombinant DNA construct. The marker can be selectable or screenable. A "selectable marker" refers to a marker that expresses a protein that allows survival of cell expressing the marker. A "screenable marker" refers to a marker that expresses a protein that provides a visible phenotype for identifying the presence of the marker. Useful selectable markers include those expressing protein that confers resistance to antibiotics such as kanamycin (nptII), hygromycin B (aph IV) and gentamycin (aac3 and aacC4) or resistance to herbicides such as glufosinate (bar or pat) and glyphosate (EPSPS). Useful screenable markers include those expressing protein that confers visual phenotype such as a gene expressing a colored or fluorescent protein such as a luciferase or green fluorescent protein (GFP) or a gene expressing a beta-glucuronidase or uidA gene (GUS) for which various chromogenic substrates are known, and those suppressing the native protein such as maize opaque 2 protein.

A recombinant DNA construct can include one or more expression cassettes, i.e. recombinant DNA for expressing specific mRNA and typically comprising a promoter element, a DNA sequence of interest, and 3' UTR. Further, an expression cassette can be arranged in any orientation capable of either facilitating expression or suppression of a gene of interest As used herein, "site specific recombination sites" means a pair of DNA segments that is recognized by a site specific recombinase in a process that allows the excision of the DNA between the pair of DNA segments. For instance, Cre recombinase recognizes either loxP recombination sites or lox511 recombination sites which are hetero-specific, which means that loxP and lox511 do not recombine together. The Cre/lox system is disclosed by Odell et al., *Plant Physiol*, 106(2): 447-58 (1994) FLP recombinase recognizes frt recombination sites as disclosed by Lyznik et al., *Nucleic Acids Res* 24(19), 3784-9 (1996). the R recombinase recognizes Rs recombination sites as disclosed by Onounchi et al., *Nucleic Acid Res.*, 19:6373-6378 (1991). The Dre recombinase recognizes rox sites as disclosed in U.S. Pat. No. 7,422,889. And, Gin recombinase recognizes gix sites as disclosed by Maeser et al., *Mol. Gen. Genet.* 230: 170-176 (1991).

An aspect of the invention is described by reference to a first pair of site specific recombination sites, e.g. loxP, recognized by a site-specific recombinase, e.g. Cre recombinase, and a second pair site specific recombination sites, e.g. lox511, also recognized by the site-specific Cre recombinase. An expression cassette can be arranged in any order or orientation that results in either the expression or suppression of the target gene of interest following recombination at one set of the heterospecific lox sites. In other aspects there is a combination of recombination systems.

As used herein, the term "operably linked" is used to describe a functional relationship between a promoter and transcribable DNA and between a transcribable DNA and 3' polyadenylation sequence.

A sequence of interest (SOI) represents polynucleotides from a gene of interest (GOI) where the polynucleotides are DNA encoding a protein. The sequence of interest is a component of the recombinant DNA constructs that is expressed in embodiments of the invention to investigate whether an expressed protein coded by an endogenous gene of interest is capable of contributing to producing a desirable phenotype or trait. In one specific aspect the invention is illustrated by using a sequence of interest that encodes the maize opaque 2 (O2) protein. The sequence of interest can be a nucleic acid sequence that causes the targeted expression, typically over-expression, of an endogenous gene. A sequence of interest is also used to design the gene suppression components of the recombinant DNA constructs that produce double-stranded RNA that can cause the inhibition of expression of an endogenous gene via natural gene silencing mechanisms. For instance, the DNA encoding protein derived from the sequence of interest (SOI) is advantageously arranged in an antisense orientation proximate to the sense oriented DNA but separated from the sense oriented DNA by recombination sites to be capable of either facilitating expression or suppression of an endogenous gene of interest depending on the presence of a recombinase.

Plant Cell Transformation Methods

Numerous methods for transforming chromosomes in a plant cell nucleus with recombinant DNA constructs are known in the art and are used in methods of preparing a transgenic plant cell and plant as generally described herein. Two effective methods for such transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), and US Patent Application Publication 2001/0042257

A1 (sugar beet), all of which are incorporated herein by reference for enabling the production of transgenic plants. Transformation of plant material is practiced in tissue culture on a nutrient media, i.e. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell can be prepared by crossing a first plant having cells with recombinant DNA construct with a second plant lacking the recombinant construct. For example, recombinant DNA can be introduced into a nucleus from a first plant line that is amenable to transformation to transgenic nucleus in cells that are grown into a transgenic plant which can be crossed with a second plant line for the introgression of the recombinant DNA into the second plant line. A transgenic plant with recombinant DNA constructs of this invention can be crossed with plant line containing DNA for expressing a recombinase that recognizes the recombination sites in the transgenic plant to modify the recombinant DNA construct by recombination. The progeny of this cross will segregate such that some of the plants will carry the DNA from both parental nucleus and some will carry DNA from one parental nucleus; such plants can be identified by markers associated with parental recombinant DNA, e.g. marker identification by analysis for recombinant DNA or, in the case where a selectable marker is linked to the recombinant. If desired, progeny plants carrying DNA from both parents can be crossed back into one parent line multiple times, for example usually 6 to 8 generations, to produce a progeny plant with substantially the same genotype as one original transgenic parental line but for the recombinant DNA of the other transgenic parental line.

In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Markers which provide an ability to visually screen transformants can also be employed.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber prior to transfer to a greenhouse or growth chamber for maturation. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA.

Transgenic Plants and Seeds

Transgenic plants derived from transgenic plant cells having a transgenic nucleus of this invention are grown to generate transgenic plants having an enhanced trait as compared to a control plant and produce transgenic seed Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein that will produce plants that will express DNA encoding protein and plants that will suppress the production of said protein with or without a selectable marker.

EXAMPLE 1

This example illustrates the design of a recombinant DNA construct that is useful in the practice of this invention. With reference to FIG. 1a, there is shown a recombinant DNA construct containing a promoter (P) operably linked to a DNA having a nucleotide sequence encoding a protein of interest for expression or suppression, i.e. designated a sequence of interest (SOI), a fragment in antisense orientation of the SOI having at least 21 nt, a pair of loxP recombination sites surrounding and bracketing the antisense fragment, and a DNA element providing polyadenylation sequence (T). The pair of loxP recombination sites is recognized by a Cre site-specific recombinase. The recombinant DNA construct is stably transformed into a corn cell which is regenerated to a transformed corn plant. In the transformed corn plant containing this construct the production of a double stranded RNA (dsRNA) transcript provides suppression of the endogenous DNA encoding protein. Without Cre recombinase, the construct is transcribed to produce a hairpin RNA that suppressed the production of the endogenous protein. When Cre recombinase is present, e.g. from crossing with a corn plant expressing the recombinase, the DNA bracketed by the loxP recombination sites is excised, i.e. the antisense fragment is removed, allowing the production of a transcript encoding the protein-. This allows the evaluation of a corn plant with over expression of the endogenous protein. The DNA construct is also transformed into cotton, rice, wheat and soybean cells which are regenerated inot plants to provide evaluation of expression and suppression of an endogenous gene from a construct in the same genetic locus.

Figure 1B:
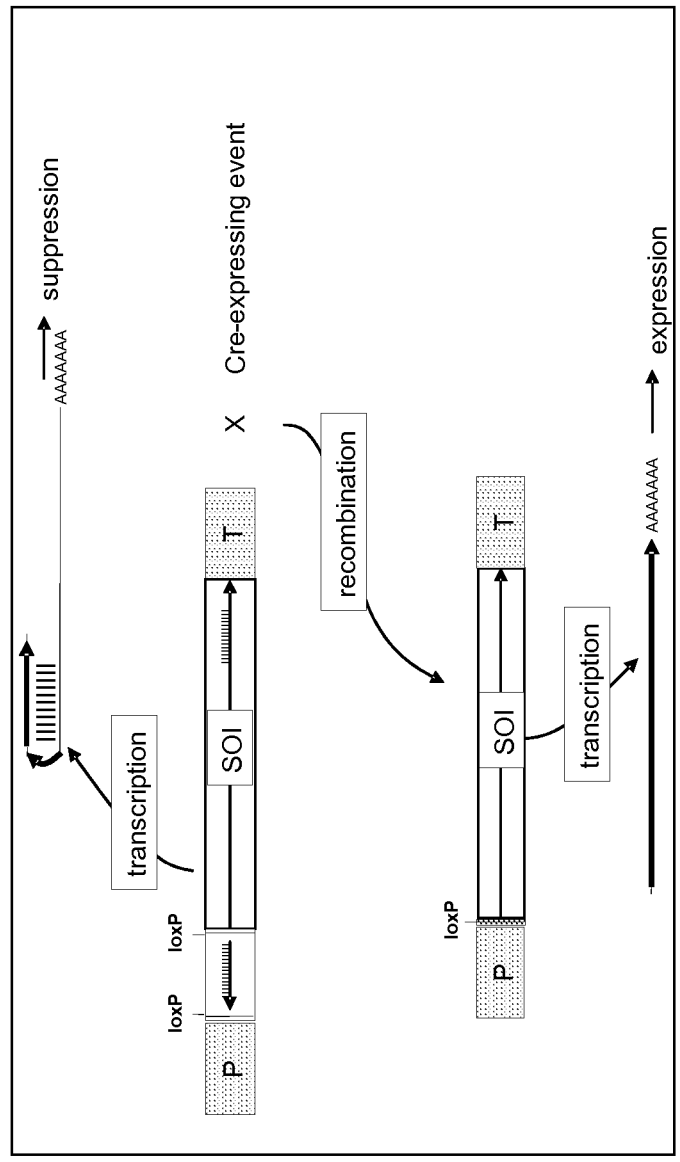

With reference to FIG. 1b, there is shown an alternative arrangement of the construct shown in FIG. 1a to achieve a similar outcome in transgenic plants and cells where the promoter (P) is followed by the antisense fragment and then the DNA encoding protein (SOI); and a pair of loxP recombination sites surround and bracket the antisense fragment as in FIG. 1a.

Figure 1C:
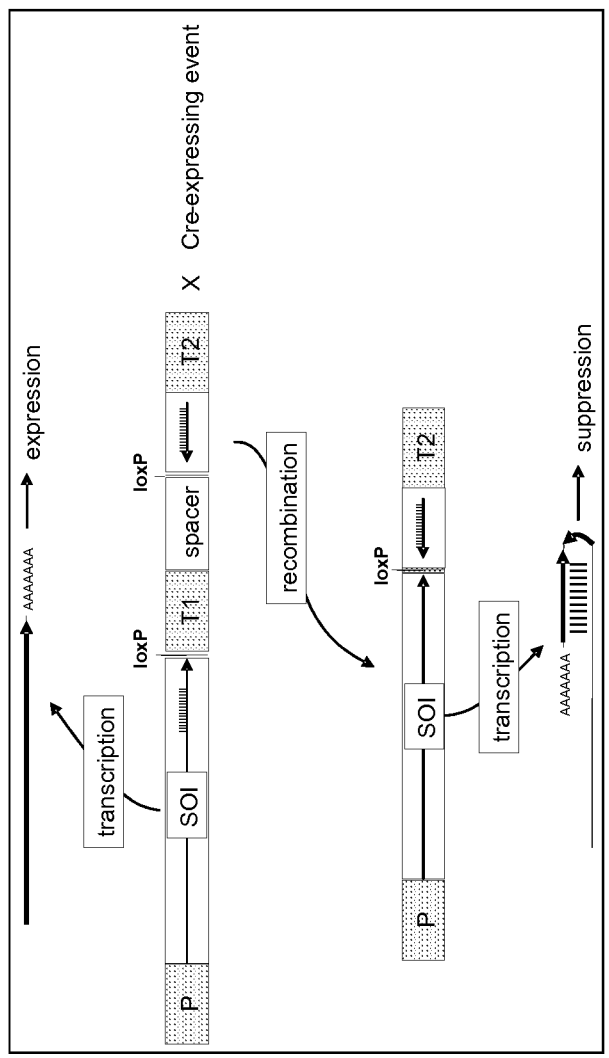

With reference to FIG. 1c there is shown a recombinant DNA construct contains a promoter (P) operably linked to a DNA having a nucleotide sequence encoding a protein of interest for expression or suppression, i.e. designated a sequence of interest (SOI), a loxP recombination site, a DNA element providing polyadenylation sequence (T1), a spacer with a length sufficient to prevent fold back and self-hybridization in RNA transcribed from the recombinant DNA construct, second loxP recombination site, antisense fragment of the SOI having at least 21 nt, and a DNA element providing a second polyadenylation sequence (T2). The pair of loxP recombination sites is surrounding and bracketing the polyadenylation sequence T1 and the spacer. Transformed plants and plant cells containing this construct result in enhanced expression of sequence of interest (SOI). Without Cre recombinase, the construct is transcribed to over express the endogenous protein. When Cre recombinase is present, e.g. from crossing with a plant expressing the recombinase, the DNA bracketed by the loxP recombination sites is excised, i.e. the first polyadenylation sequence, T1 and the spacer fragment are removed, allowing the evaluation of a plant with suppression of the endogenous protein.

EXAMPLE 2

Figure 2A:
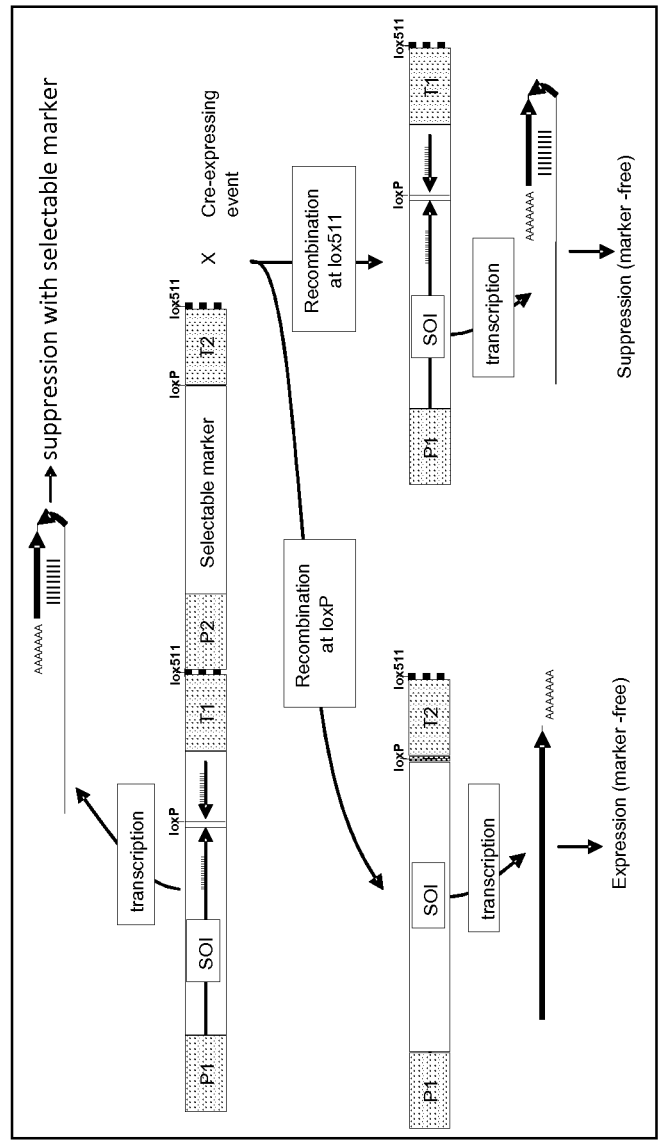
FIGS. 2a and 2b are described in detail in Example 2.

With reference to FIG. 2a there is shown a recombinant DNA construct with two expression cassettes. More specifically the construct contains a promoter (P1) operably linked to DNA having a nucleotide sequence encoding a protein of interest for expression or suppression, i.e. designated a sequence of interest (SOI), a loxP recombination site, an antisense fragment of the DNA encoding the endogenous protein, DNA providing a first polyadenylation sequence (T1), a lox511 recombination site, a second promoter (P2) operably linked to a DNA encoding a selectable marker, a second loxP recognition site, DNA providing second polyadenylation sequence (T2) and a second lox511 recognition site. The first pair of recombination sites, i.e. the loxP sites, is surrounding and bracketing the antisense fragment, the first polyadenylation sequence (T1), the first lox511 site, the second promoter (P2) and the DNA encoding selectable marker. The second pair of recombination sites i.e. the lox511 sites, is surrounding and bracketing the selectable marker expression cassette, and the second loxP site. The recombinant DNA construct is stably transformed into a corn cell which is regenerated to a transformed corn plant. In the transformed corn plants containing this construct results in production of a double stranded RNA (dsRNA) transcript that provides suppression of the endogenous DNA encoding protein (SOI) with expression of selectable marker protein. When transformed plant is crossed to a plant expressing a Cre recombinase, either of the pairs of the recombination sites can be involved in recombination. When the loxP sites are recombined, antisense fragment, first polyadenylation sequence (T1), the first lox511 site, the second promoter (P2) and the DNA encoding selectable marker are removed allowing for over expression of the endogenous protein. When the lox511 sites are recombined, the selectable marker expression cassette is removed allowing for transcription of RNA that forms a dsRNA for suppression of the endogenous protein.

The DNA construct is also transformed into cotton, rice, wheat and soybean cells which are regenerated into plants to provide evaluation of expression and suppression of an endogenous gene from a construct in the same genetic locus.

Figure 2B:
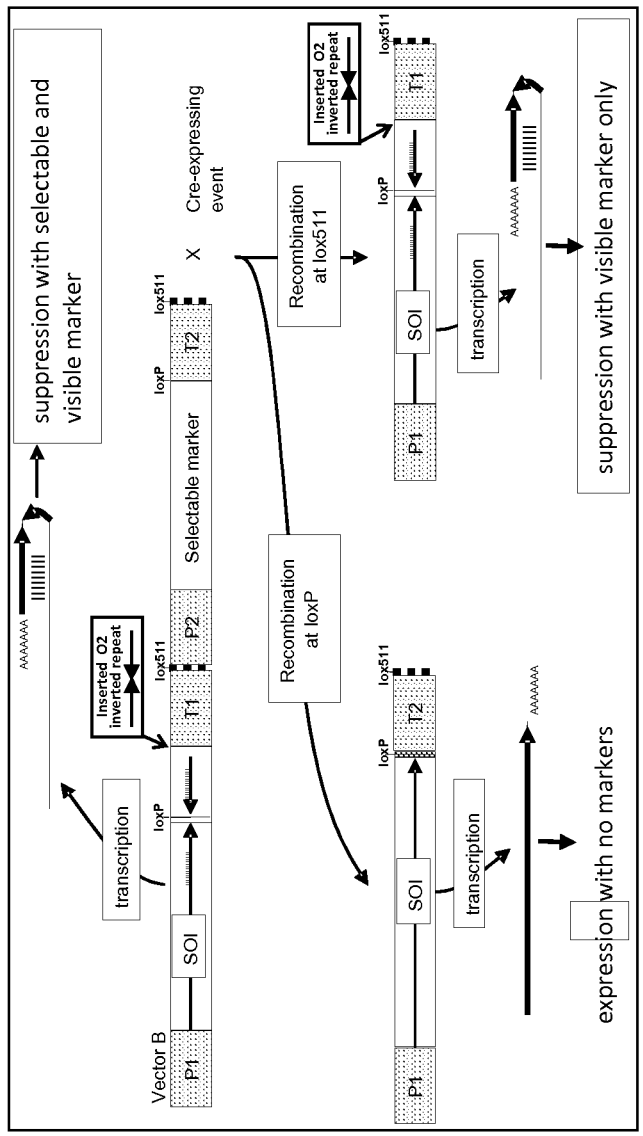

With reference to FIG. 2b there is shown a recombinant DNA construct similar to that of FIG. 2a with an additional DNA encoding a screenable marker, e.g., as an inverted repeat of DNA for suppressing corn opaque 2 gene. The inverted repeat DNA is located adjacent to the antisense fragment. The inverted repeat DNA functions to suppress a gene that provides a visible phenotype, e.g. DNA for suppressing the opaque 2 gene. Stable integration of recombinant DNA into plant will allow a visual phenotype indicating desired suppression of DNA encoding for a screenable marker. When transformed plant is crossed to a plant expressing a Cre recombinase, either of the pairs of the recombination sites can be involved in recombination. When the loxP sites are recombined, antisense fragment, inverted repeat of DNA, first polyadenylation sequence (T1), the first lox511 site, the second promoter (P2) and the DNA encoding selectable marker are removed allowing for over expression the endogenous protein. When the lox511 sites are recombined, the selectable marker expression cassette is removed allowing suppression of the gene that provides visible phenotype, e.g. DNA for suppressing the opaque 2 gene.

EXAMPLE 3

Figure 3A:
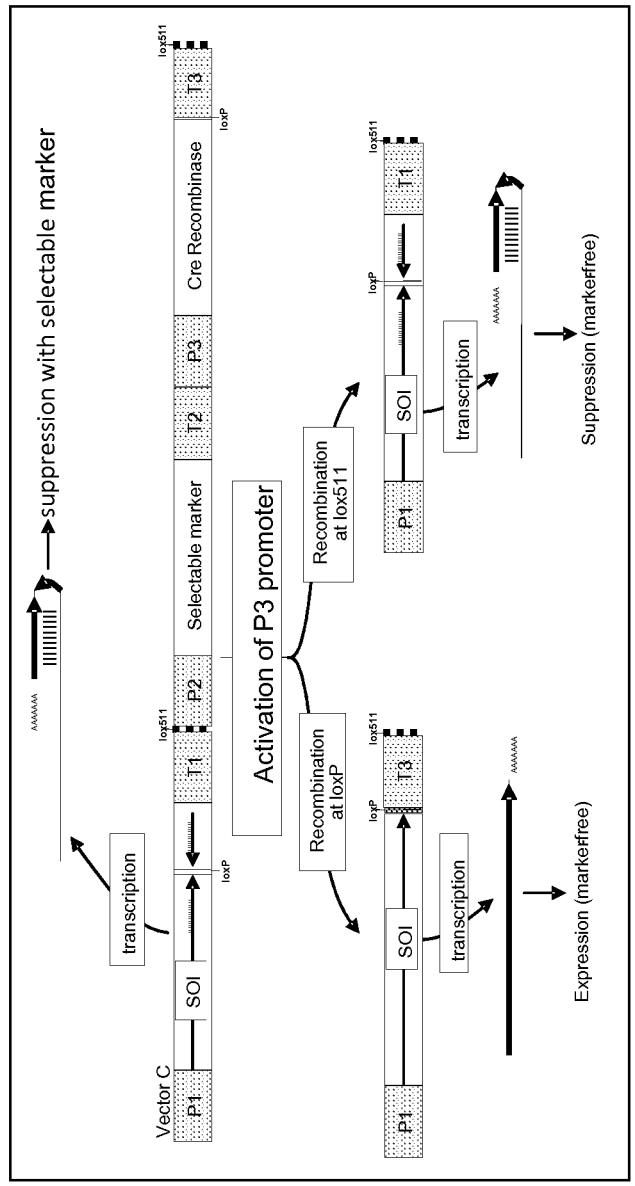
FIGS. 3a and 3b are described in detail in Example 3.

With reference to FIG. 3a there is shown a recombinant DNA construct containing three cassettes. More specifically, the construct contains a a promoter (P1) operably linked to DNA encoding protein i.e. designated a sequence of interest (SOI), a loxP recombination site, antisense fragment of the DNA encoding protein, DNA providing a first polyadenylation sequence (T1), a lox511 recombination site, a second promoter (P2) operably linked to a DNA encoding a selectable marker, DNA providing second polyadenylation sequence (T2), a third promoter (P3) operably linked to a DNA encoding a Cre recombinase, second loxP recombination site, DNA providing third polyadenylation sequence (T3) and a second lox511 recognition site. It is important that the third promoter (P3) not be constitutive. Useful P3 promoters are chemically inducible promoter that are regulated by external agent. See Wang et al., "Chemically regulated expression nsystems and their applications n transgenic plants", Transgenic Research, 12:529-540, 2003 for a disclosure of copper-inducible promoters and glucocorticoid-inducible promoters. The first pair of recombination sites, i.e. the loxP sites, is surrounding and bracketing the antisense fragment, the first polyadenylation sequence (T1), the first lox511 site, selectable marker expression cassette, third promoter (P3) and DNA encoding for Cre recombinase. The second pair of recombination sites, i.e. the lox511 sites, is surrounding and bracketing the selectable marker expression cassette, the Cre recombinase expression cassette and the second loxP site. The recombinant DNA construct is stably transformed into a corn cell which is regenerated to a transformed corn plant. In the transformed corn plants containing this construct result in production of a double stranded RNA (dsRNA) transcript that provides suppression of the endogenous DNA encoding protein (SOI) with expression of selectable marker protein. When transformed plant expressing a Cre recombinase by activation of P3, either of the pairs of the recombination sites can be involved in recombination. When the loxP sites are recombined, antisense fragment, first polyadenylation sequence (T1), the first lox511 site, selectable marker expression cassette, third promoter (P3) and the DNA encoding for Cre recombinase are removed allowing for over expression of the endogenous protein. When the lox511 sites are recombined, the selectable marker expression cassette and Cre recombinase expression cassette are removed allowing for transcription of RNA that forms a dsRNA for suppression of the endogenous protein.

The DNA construct is also transformed into cotton, rice, wheat and soybean cells which are regenerated into plants to provide evaluation of expression and suppression of an endogenous gene from a construct in the same genetic locus.

Figure 3B:
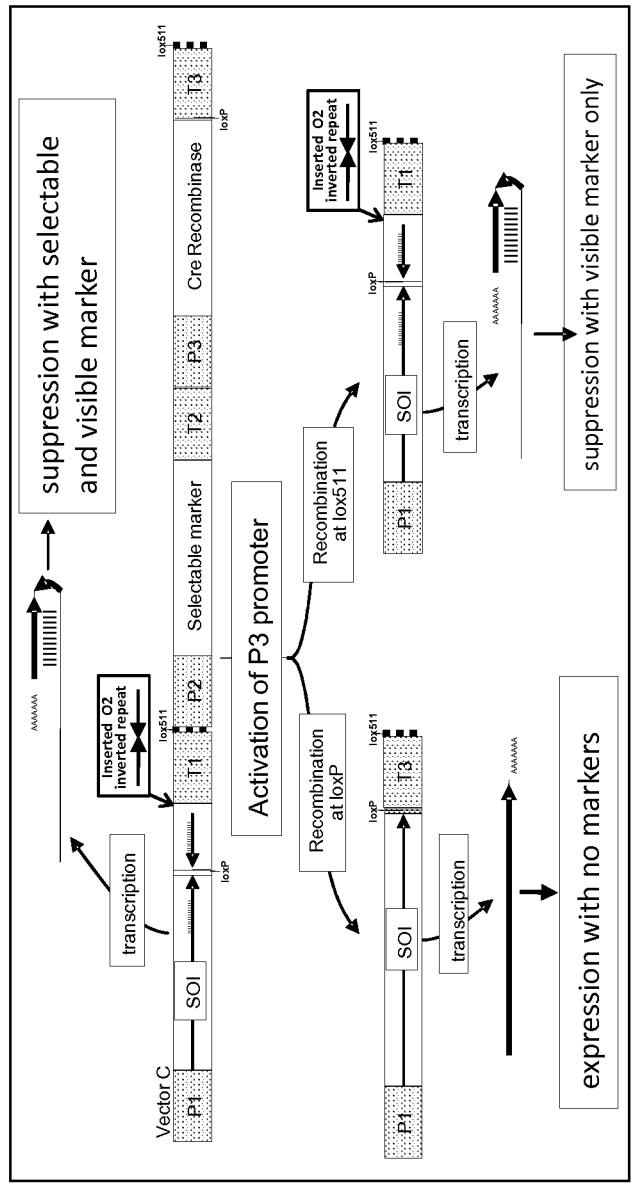

With reference to FIG. 3b there is shown a recombinant DNA construct similar to that of FIG. 3a with an additional DNA encoding a screenable marker, e.g., as an inverted repeat of DNA for suppressing corn opaque 2 gene. The inverted repeat DNA is located adjacent to the antisense fragment. The inverted repeat DNA functions to suppress a gene that provides a visible phenotype, e.g. DNA for suppressing the opaque 2 gene. Stable integration of recombinant DNA into plant will allow a visual phenotype indicating desired suppression of DNA encoding for a screenable marker. When transformed plant expressing a Cre recombinase by activation of P3, either of the pairs of the recombination sites can be involved in recombination, either of the pairs of the recombination sites can be involved in recombination. When the loxP sites are recombined, antisense fragment, inverted repeat of DNA, first polyadenylation sequence (T1), the first lox511 site, selectable marker expression cassette, third promoter (P3) and the DNA encoding Cre recombinase are removed allowing for over expression of the gene that provides visible phenotype, e.g. DNA for the opaque 2 gene. When the lox511 sites are recombined, the selectable marker expression cassette, third promoter (P3) and the DNA encoding for Cre recombinase are removed allowing suppression of the gene that provides visible phenotype, e.g. DNA for suppressing the opaque 2 gene. This allows the evaluation of enhanced expression and suppression for the DNA encoding screenable marker.

EXAMPLE 4

Figure 4A:
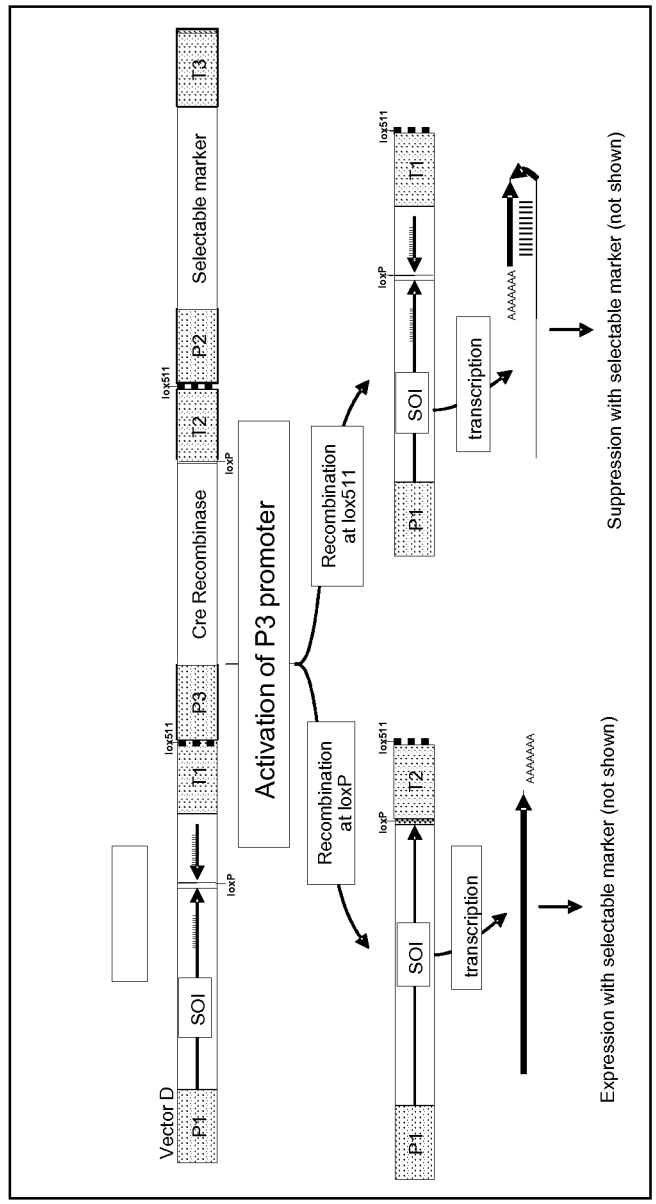
FIGS. 4a and 4b are described in detail in Example 4.

With reference to FIG. 4a there is shown a recombinant DNA construct containing three cassettes. More specifically, the construct contains a promoter (P1) operably linked to DNA encoding protein, i.e. designated a sequence of interest (SOI), a loxP recombination site, antisense fragment of the DNA encoding protein, DNA providing a first polyadenylation sequence (T1), a lox511 recombination site, a promoter (P3) operably linked to a DNA encoding a Cre recombinase, second loxP recombination site, DNA providing polyadenylation sequence (T3), second lox511 recognition site, a promoter (P2) operably linked to a DNA encoding a selectable marker, and a polyadenylation sequence (T2). An advantage of the construct illustrated in FIG. 4 is that the third promoter (P3) is constitutive. The first pair of recombination sites, i.e. the loxP sites, is surrounding and bracketing the antisense fragment, the first polyadenylation sequence (T1), the first lox511 site, promoter (P3) and DNA encoding for Cre recombinase. The second pair of recombination sites, i.e. the lox511 sites, is surrounding and bracketing the Cre recombinase expression cassette along with second loxP site. The recombinant DNA construct is stably transformed into a corn cell which is regenerated to a transformed corn plant. In the transformed corn plants containing this construct result in production of a double stranded RNA (dsRNA) transcript that provides suppression of the endogenous DNA encoding protein (SOI) with expression of selectable marker protein. When a transformed plant expressing a Cre recombinase, either of the pairs of the recombination sites can be involved in recombination. When the loxP sites are recombined, antisense fragment, first polyadenylation sequence (T1), the first lox511 site, promoter (P3), and DNA encoding for Cre recombinase are removed allowing for over expression of the endogenous protein. When the lox511 sites are recombined, the Cre recombinase expression cassette is removed allowing for transcription of RNA that forms a dsRNA for suppression of the endogenous protein.

The DNA construct is also transformed into cotton, rice, wheat and soybean cells which are regenerated into plants to provide evaluation of expression and suppression of an endogenous gene from a construct in the same genetic locus.

Figure 4B:
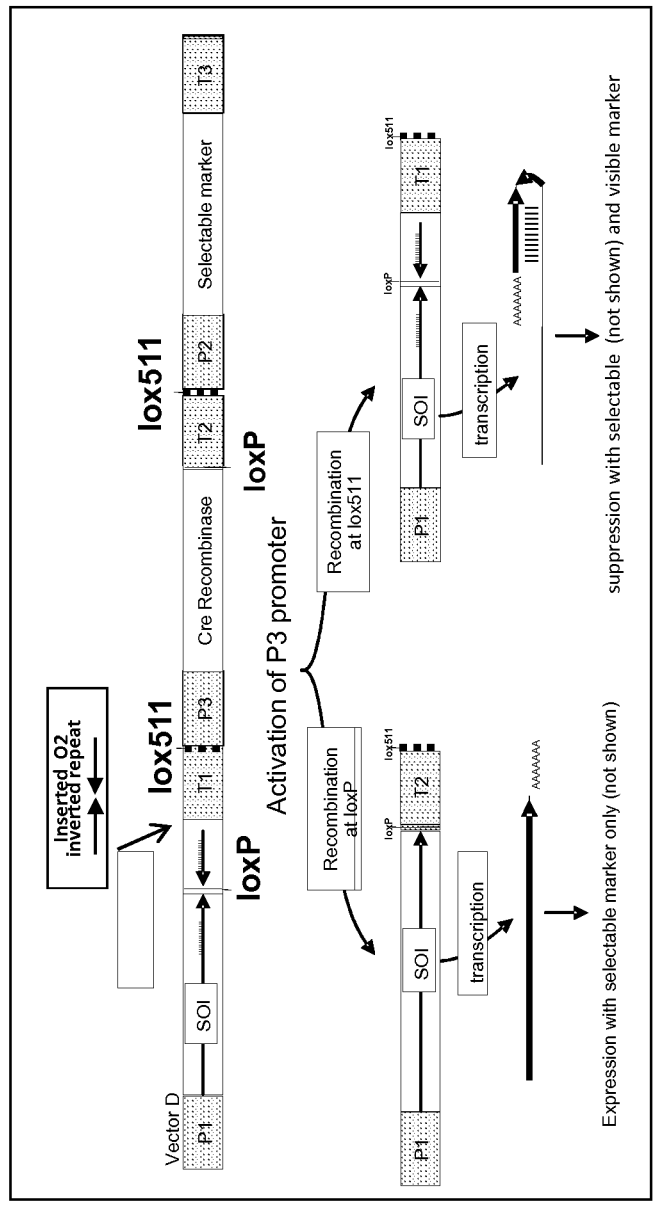

With reference to FIG. 4b there is shown a recombinant DNA construct similar to that of FIG. 4a with an additional DNA encoding a screenable marker comprising an inverted repeat of DNA for suppressing corn opaque 2 gene to is the inverted repeat DNA is located adjacent to the antisense fragment. Stable integration of the recombinant DNA into a plant will allow a visual phenotype with the screenable marker indicating the suppression of the endogenous gene. When a transformed plant expressing a Cre recombinase, either of the pairs of the recombination sites can be involved in recombination. When the loxP sites are recombined, antisense DNA encoding the endogenous protein(SOI), inverted repeat, and DNA encoding recombinase are removed allowing expression of DNA encoding protein (SOI) without indication from the screenable marker When lox511 sites are recombined, Cre recombinase expression cassette and second loxP site are removed allowing suppression of the protein (SOI) with visible indication from the selectable marker.

We claim:
1. A recombinant DNA molecule comprising:
 (a) a first DNA segment comprising
  (i) a first promoter operably linked to a sense-oriented sequence of interest;
  (ii) a first member of a first pair of recombination sites;
  (iii) an antisense fragment of said sequence of interest;
  (iv) DNA providing a first polyadenylation sequence; and
  (v) a first member of a second pair of recombination sites;
 (b) a second DNA segment comprising
  (i) a second promoter operably linked to DNA encoding a selectable marker; and
  (ii) DNA providing a second polyadenylation sequence;
 (c) a second member of said first pair of recombination sites, located 3' to said DNA encoding a selectable marker; and
 (d) a second member of said second pair of recombination sites, located 3' to said DNA providing a second polyadenylation sequence,
 wherein said first and second pairs of recombination sites are different.

2. The recombinant DNA molecule of claim 1, wherein said second member of said first pair of recombination sites is located between said DNA encoding a selectable marker and said DNA providing a second polyadenylation sequence, and wherein said second member of said second pair of recombination sites is located 3' and adjacent to said DNA providing a second polyadenylation sequence.

3. The recombinant DNA molecule of claim 1, further comprising a third segment comprising
 (i) a third promoter operably linked to DNA encoding a site-specific recombinase; and
 (ii) DNA providing a third polyadenylation sequence,
wherein said second member of said first pair of recombination sites is located between said DNA encoding said site-specific recombinase and said DNA providing a third polyadenylation sequence, and wherein said second member of said second pair of recombination sites is located 3' and adjacent to said DNA providing a third polyadenylation sequence.

4. The recombinant DNA molecule of claim 1, wherein said recombinant DNA molecule is capable of suppressing the expression of an endogenous gene comprising said sequence of interest in a cell in the absence of a site-specific recombinase that recognize said first or second pair of recombination sites.

5. The recombinant DNA molecule of claim 1, wherein the recombination of said first pair of recombination sites excises said DNA encoding a selectable marker and enhance the expression of said sequence of interest.

6. The recombinant DNA molecule of claim 1, wherein the recombination of said second pair of recombination sites excises said DNA encoding a selectable marker and suppress the expression of an endogenous gene comprising said sequence of interest.

7. The recombinant DNA molecule of claim 1, wherein said sequence of interest encodes a protein of interest.

8. The recombinant DNA molecule of claim 1, wherein said first and second pairs of recombination sites are heterospecific.

9. The recombinant DNA molecule of claim 1, wherein said first or second pair of recombination sites are 1oxP or 1ox511 recombination sites.

10. The recombinant DNA molecule of claim 1, wherein said first and second pairs of recombination sites are selected from the group consisting of lox sites for recombination with Cre recombinase, Frt sites for recombination with Flp recombinase, Rs sites for recombination with R recombinase, rox sites for recombination with Dre recombinase, and gix sites for recombination with Gin recombinase.

11. The recombinant DNA molecule of claim 1, wherein said antisense fragment of said sequence of interest is at least 21 nucleotides in length.

12. The recombinant DNA molecule of claim 1, further comprising DNA encoding a visible marker.

13. The recombinant DNA molecule of claim 12, wherein said visible marker is adjacent to antisense fragment of said sequence of interest.

14. The recombinant DNA molecule of claim 12, wherein said visible marker is from suppression of a opaque 2 gene.

15. The recombinant DNA molecule of claim 3, wherein said third promoter is selected from the group consisting of a constitutive promoter, a non-constitutive promoter, an inducible promoter, and a chemically inducible promoter.

16. A transgenic plant comprising the recombinant DNA molecule of claim 1.

17. The transgenic plant of claim 16, wherein said plant is selected from the group consisting of soybean, corn, wheat, rice, cotton, canola, and sugar beet.

18. The transgenic plant of claim 16, said transgenic plant comprising an altered property relative to a plant lacking said recombinant DNA molecule.

19. A method of producing a population of transgenic plants, said method comprising:
   transforming a plant cell with the recombinant DNA molecule of claim 1, producing a primary transgenic plant from said plant cell, collecting transgenic seeds from said primary transgenic plant, and growing said transgenic seeds to produce a population of transgenic plants, wherein said population of transgenic plants comprise both plants with overexpression of said sequence of interest and plants with suppression of an endogenous gene comprising said sequence of interest.

20. The method of claim 19, further comprising:
   crossing said primary transgenic plant with another plant expressing a site-specific recombinase.

21. A population of transgenic plants produced from a common parent plant, wherein said population comprises plants having overexpression of a sequence of interest and plants having suppression of an endogenous gene comprising said sequence of interest, wherein said common parent plant comprises said recombinant DNA molecule of claim 1, wherein the parent plant is homozygous for said recombinant DNA molecule.

* * * * *